US008198089B2

(12) United States Patent
Akada et al.

(10) Patent No.: US 8,198,089 B2
(45) Date of Patent: Jun. 12, 2012

(54) FLOCCULENT YEAST AND METHOD FOR PRODUCTION THEREOF

(75) Inventors: Rinji Akada, Yamaguchi (JP); Sanom Nonklang, Yamaguchi (JP); Hisashi Hoshida, Yamaguchi (JP); Babiker Mohamed Ahmed Abdel-Banat, Yamaguchi (JP)

(73) Assignee: Yamaguchi University, Yamaguchi (JP)

( * ) Notice: Subject to any disclaimer, the term of this patent is extended or adjusted under 35 U.S.C. 154(b) by 0 days.

(21) Appl. No.: 12/922,602

(22) PCT Filed: Mar. 18, 2009

(86) PCT No.: PCT/JP2009/001214
§ 371 (c)(1),
(2), (4) Date: Sep. 14, 2010

(87) PCT Pub. No.: WO2009/116286
PCT Pub. Date: Sep. 24, 2009

(65) Prior Publication Data
US 2011/0020937 A1  Jan. 27, 2011

(30) Foreign Application Priority Data
Mar. 18, 2008 (JP) ................................. 2008-069329
Jul. 18, 2008 (JP) ................................. 2008-187206

(51) Int. Cl.
*C12N 15/70* (2006.01)
*C12N 1/19* (2006.01)
*C12N 1/00* (2006.01)
(52) U.S. Cl. ................. 435/471; 435/254.2; 435/255.1
(58) Field of Classification Search .................... None
See application file for complete search history.

(56) References Cited

U.S. PATENT DOCUMENTS
2005/0084848 A1* 4/2005 Phillips .............................. 435/6

FOREIGN PATENT DOCUMENTS
| JP | 02-000476 | | 1/1990 |
| JP | 08-266287 | B2 | 10/1996 |
| JP | 10-234368 | A | 9/1998 |
| JP | 7-509372 | T | 10/2005 |
| JP | 2005-532055 | A | 10/2005 |
| JP | 2006-174767 | A | 7/2006 |
| JP | 2006-325577 | A | 12/2006 |
| JP | 2007-195406 | A | 8/2007 |
| WO | WO2004005491 | * | 1/2004 |

OTHER PUBLICATIONS

Suzuki, O. et al., "Utilization of Thermotolerant and flocculent Yeast for Wastewater Treatment", Hakko Kogaku Kaishi, 69, 2, 83-87, (1991).
"Abstracts of the Articles Printed in Hakkokogaku Kaishi, Inactivating Effect of Basic Tripeptide Derivatives on Phages,", Satoh, Ken-ichi et al. :vol. 69, No. 2 (1991).
Almeida, et al.: "Acquisition of flocculation phenotype by *Kluyveromyces marxianus* when overexpressing GAP1 gene encoding an isoform of glyceraldenhyde-3-phosphate dhydrogenase", Journal of Microbiological Methods 55 (2003) 433-440.
Bussey, Howard et al.: "The nucleotide sequence of chromosome I from *Saccharomyces cerevisiae*", Proc. Natl. Acad. Sci. USA, vol. 92, 3809-3813, Apr. 1995.
Cunha, A. F. et al.: "Control by sugar of *Saccharomyces cerevisiae* flocculation for industrial ethanol production", FEMS Yeast Res., (2006), vol. 6, 280-287.
Dietrich, F.S. et al.: "The nucleotide sequence of *Saccharomyces cerevisiae* chromosome V", Nature, vol. 387, Supp, 78-81, May 29, 1997.
Dujon B. et al.: "Complete DNA sequence of yeast chromosome XI", Nature, vol. 369, Jun. 2, 1994.
Johnston, M. et al: "Complete Nucleotide Sequence of *Saccharomyces cerevisiae* Chromosome VIII", Science: Sep. 30, 1994; 265, 5181, 2077-2082.
Kuroda, S. et al.: "Fermentalbe and nonfermental carbon sources sustained constitutive levels of expression of yeast triosephosphate dehydrogenase 3 gene rom distinct promoter elements", J. Biol. Chem., (1994), vol. 269, No. 8, pp. 6153-6162.
Kuroda, Shun'chi et al.: "Efficient expression of genetically engineered hepatitis B virus surface antigen P31 proteins in yeast" Gene. 78 (1989) 297-308.
Lertwattanasakul, Noppon et al.: "Comparison of the Gene Expression Patterns of Alcohol Dehydrogenase Isozymes in the Thermotolerant Yeast *Kluyversmyces marxianus* and Their Physiological Functions" *Biosci. Biotechnol. Biochem.*, 71 (5), 1170-1182, 2007.
Lundblad, V. et al.: "Manipulation of cloned yeast DNA", Current Protocols in Mol. Biol., (1997), Unit 13, 10. 1-13.10.14.
Nedeva, T.S. et al.: "Screening of thermotolerant yeasts as producers of superoxide dismutase" FEMS Microbiology Letters 107 (1993) 49-52.
Suzuki, O. et al., "Fermentable and nonfermentable carbon sources sustain constitutive levels of expression of yeast triosephosphate dehydrogenase 3 gene from distinct promotor elements", J. Biol. Chem., (1994), vol. 269, No. 8, 6153-6162.
Teunissen A.W.R.H. et al. "Sequence of the Open Reading Frame of the FL01 Gene from *Saccharomyces cerevisiae*", Yeast, vol. 9: 423-427 (1993).

(Continued)

*Primary Examiner* — Michele K Joike
(74) *Attorney, Agent, or Firm* — Venable LLP.; Nancy J. Axelrod; Robert Kinberg

(57) ABSTRACT

It is to provide a novel *Kluyveromyces marxianus* transformant having thermotolerance and flocculation property, suitable for the industrial production of bioethanol, by introducing a foreign flocculation gene into *Kluyveromyces marxianus*, and an efficient method for producing the transformant. The present inventors focused on the flocculation gene FLO of *Saccharomyces cerevisiae* as a foreign gene to confer flocculation property to *Kluyveromyces marxianus* and produced a linear DNA fragment comprising a known expression promoter sequence and a FLO gene sequence derived from *Saccharomyces cerevisiae*. As a result of introducing this linear DNA fragment into *Kluyveromyces marxianus*, the present inventors have confirmed that *Kluyveromyces marxianus* transformant can be obtained efficiently, and that the flocculation property of the above transformant is unexpectedly and significantly enhanced. The present invention has been thus completed.

10 Claims, 7 Drawing Sheets

OTHER PUBLICATIONS

Wang, Fu-Zhuan et al.: "Construction of a Flocculating Yeast for Fuel Ethanol Production", Biotechnol Lett (2008) 30:97-102.

Almeida, C. et al.: "Acquisition of flocculation phenotype by *Kluyveromyces marxianus* when overexpressing GAP1 gene encoding an isoform of glyceraldenhyde-3-phosphate dhydrogenase", Journal of Microbiological Methods 55 (2003) 433-440.

Kuroda, S. et al.: "Fermentable and nonfermentable carbon sources sustain constitutive levels of expression of yeast triosephosphate dehydrogenase 3 gene from distinct promoter elements", J. Biol. Chem., (1994), vol. 269, No. 8, pp. 6153-6162.

Abdel-Banat, B.M.A. et al., "High-temperature fermentation: how can processes for ethanol production at high temperatures become superior to the traditional process using mesophilic yeast?" Appl. Microbiol. Biotechnol. (2010) 85:861-867.

Nonklang, S. et al., "Construction of Flocculent Kluyveromyces marxianus Strains Suitable for High-Temperature Ethanol Fermentation," Biosci. Biotechnol. Biochem. (2009) 73(3), 10901095.

Supplementary European Search Report to Application EP 09 72 1406, dated Jan. 13, 2012.

* cited by examiner

Time of the heat shock

Kluyveromyces marxianus strain

SEQUENCE LISTING

```
<160> NUMBER OF SEQ ID NOS: 29

<210> SEQ ID NO 1
<211> LENGTH: 40
<212> TYPE: DNA
<213> ORGANISM: Saccharomyces cerevisiae
<220> FEATURE:
<221> NAME/KEY: gene
<222> LOCATION: (1)..(40)
<223> OTHER INFORMATION: FLO1

<400> SEQUENCE: 1
atgacaatgc ctcatcgcta tatgtttttg gcagtcttta                    40

<210> SEQ ID NO 2
<211> LENGTH: 40
<212> TYPE: DNA
<213> ORGANISM: Saccharomyces cerevisiae
<220> FEATURE:
<221> NAME/KEY: gene
<222> LOCATION: (1)..(40)
<223> OTHER INFORMATION: FLO5

<400> SEQUENCE: 2
atgacaattg cacaccactg catattttg gtaatcttgg                     40

<210> SEQ ID NO 3
<211> LENGTH: 40
<212> TYPE: DNA
<213> ORGANISM: Saccharomyces cerevisiae
<220> FEATURE:
<221> NAME/KEY: gene
<222> LOCATION: (1)..(40)
<223> OTHER INFORMATION: FLO9
```

```
<400> SEQUENCE: 3
atgtctctgg cacattattg tttactacta gccatcgtca                          40

<210> SEQ ID NO 4
<211> LENGTH: 40
<212> TYPE: DNA
<213> ORGANISM: Saccharomyces cerevisiae
<220> FEATURE:
<221> NAME/KEY: gene
<222> LOCATION: (1)..(40)
<223> OTHER INFORMATION: FLO10

<400> SEQUENCE: 4
atgcctgtgg ctgctcgata tatattttg accggcctat                           40

<210> SEQ ID NO 5
<211> LENGTH: 50
<212> TYPE: DNA
<213> ORGANISM: Artificial Sequence
<220> FEATURE:
<223> OTHER INFORMATION: primer: FLO1-401

<400> SEQUENCE: 5 tattttaat tcttgtcacc agtaaacaga acatccaaaa ggcgcgcccg                50

<210> SEQ ID NO 6
<211> LENGTH: 50
<212> TYPE: DNA
<213> ORGANISM: Artificial Sequence
<220> FEATURE:
<223> OTHER INFORMATION: primer: FLO1-402

<400> SEQUENCE: 6
taaagactgc caaaaacata tagcgatgag gcattgtcat tttatgtgat                50

<210> SEQ ID NO 7
<211> LENGTH: 50
<212> TYPE: DNA
<213> ORGANISM: Artificial Sequence
<220> FEATURE:
<223> OTHER INFORMATION: primer: FLO5-401

<400> SEQUENCE: 7
caaatgattt tctttaaatt gattagcacc actaaaaaaa ggcgcgcccg                50

<210> SEQ ID NO 8
<211> LENGTH: 50
<212> TYPE: DNA
<213> ORGANISM: Artificial Sequence
<220> FEATURE:
<223> OTHER INFORMATION: primer: FLO5-402

<400> SEQUENCE: 8
ccaagattac caaaaatatg cagtggtgtg caattgtcat tttatgtgat                50

<210> SEQ ID NO 9
<211> LENGTH: 50
<212> TYPE: DNA
<213> ORGANISM: Artificial Sequence
<220> FEATURE:
<223> OTHER INFORMATION: primer: FLO9-401

<400> SEQUENCE: 9
gcaatttaaa aagaacaatt gtacaataaa agccccaaaa ggcgcgcccg                50
```

```
<210> SEQ ID NO 10
<211> LENGTH: 50
<212> TYPE: DNA
<213> ORGANISM: Artificial Sequence
<220> FEATURE:
<223> OTHER INFORMATION: primer: FLO9-402

<400> SEQUENCE: 10
tgacgatggc tagtagtaaa cataatgtg ccagagacat tttatgtgat               50

<210> SEQ ID NO 11
<211> LENGTH: 50
<212> TYPE: DNA
<213> ORGANISM: Artificial Sequence
<220> FEATURE:
<223> OTHER INFORMATION: primer: FLO10-401

<400> SEQUENCE: 11
tttgttttag ggtgcttaat caaagaacaa caaataaaaa ggcgcgcccg               50

<210> SEQ ID NO 12
<211> LENGTH: 50
<212> TYPE: DNA
<213> ORGANISM: Artificial Sequence
<220> FEATURE:
<223> OTHER INFORMATION: primer: FLO10-402

<400> SEQUENCE: 12
ataggccggt caaaaatata tatcgagcag ccacaggcat tttatgtgat               50

<210> SEQ ID NO 13
<211> LENGTH: 22
<212> TYPE: DNA
<213> ORGANISM: Artificial Sequence
<220> FEATURE:
<223> OTHER INFORMATION: primer: FLO1-517

<400> SEQUENCE: 13
gaattctagc cttcctctgc tc                                              22

<210> SEQ ID NO 14
<211> LENGTH: 22
<212> TYPE: DNA
<213> ORGANISM: Artificial Sequence
<220> FEATURE:
<223> OTHER INFORMATION: primer: FLO1/5 415c

<400> SEQUENCE: 14
ctagggttac gtttgttggg gt                                              22

<210> SEQ ID NO 15
<211> LENGTH: 22
<212> TYPE: DNA
<213> ORGANISM: Artificial Sequence
<220> FEATURE:
<223> OTHER INFORMATION: primer: FLO5-413

<400> SEQUENCE: 15
ggcaccctcg agaattacac tt                                              22

<210> SEQ ID NO 16
<211> LENGTH: 22
<212> TYPE: DNA
<213> ORGANISM: Artificial Sequence
<220> FEATURE:
<223> OTHER INFORMATION: primer: FLO9-362
```

```
<400> SEQUENCE: 16
gtacatcaca cacgaccaca ga                                          22

<210> SEQ ID NO 17
<211> LENGTH: 22
<212> TYPE: DNA
<213> ORGANISM: Artificial Sequence
<220> FEATURE:
<223> OTHER INFORMATION: primer: FLO9-455c

<400> SEQUENCE: 17
taagaacccg tctgtggtgg ta                                          22

<210> SEQ ID NO 18
<211> LENGTH: 22
<212> TYPE: DNA
<213> ORGANISM: Artificial Sequence
<220> FEATURE:
<223> OTHER INFORMATION: primer: FLO10-311

<400> SEQUENCE: 18
gttgtttggt atgtatccgc cg                                          22

<210> SEQ ID NO 19
<211> LENGTH: 22
<212> TYPE: DNA
<213> ORGANISM: Artificial Sequence
<220> FEATURE:
<223> OTHER INFORMATION: primer: FLO10-284c

<400> SEQUENCE: 19
gcacaagtat ctgatgcgcc at                                          22

<210> SEQ ID NO 20
<211> LENGTH: 25
<212> TYPE: DNA
<213> ORGANISM: Artificial Sequence
<220> FEATURE:
<223> OTHER INFORMATION: primer: FLO1-5037c

<400> SEQUENCE: 20
aagttggcga tggttcatta attgc                                       25

<210> SEQ ID NO 21
<211> LENGTH: 25
<212> TYPE: DNA
<213> ORGANISM: Artificial Sequence
<220> FEATURE:
<223> OTHER INFORMATION: primer: FLO5-3759c

<400> SEQUENCE: 21
gtactgcgtg tggcatgtaa gcagc                                       25

<210> SEQ ID NO 22
<211> LENGTH: 25
<212> TYPE: DNA
<213> ORGANISM: Artificial Sequence
<220> FEATURE:
<223> OTHER INFORMATION: primer: FLO9-4454c

<400> SEQUENCE: 22
actagatctt acgttagtac tgctg                                       25
```

<210> SEQ ID NO 23
<211> LENGTH: 25
<212> TYPE: DNA
<213> ORGANISM: Artificial Sequence
<220> FEATURE:
<223> OTHER INFORMATION: primer: FLO10-3980c

<400> SEQUENCE: 23
cgccgggcag tagtaactat tgtta                                25

<210> SEQ ID NO 24
<211> LENGTH: 26
<212> TYPE: DNA
<213> ORGANISM: Artificial Sequence
<220> FEATURE:
<223> OTHER INFORMATION: primer

<400> SEQUENCE: 24
atcaaagaag gttaatgtgg ctgtgg                               26

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
ttcgtcatta tagaaatcat tacgac                               26

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
gaagagtatt gagaagggca ac                                   22

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
tgttgtgaag tcattgacac ag                                   22

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
tactaggaaa tgagaatttt tggaa                                25

<210> SEQ ID NO 29
<211> LENGTH: 25
<212> TYPE: DNA
<213> ORGANISM: Artificial Sequence
<220> FEATURE:
<223> OTHER INFORMATION: primer

```
<400> SEQUENCE: 29
tgcgattggc agtggaacag tggta                                                25
```

FLOCCULENT YEAST AND METHOD FOR PRODUCTION THEREOF

This application is a U.S. national stage application of PCT/JP2009/001214, filed Mar. 18, 2009, and claims priority to Japanese patent application no. 2008-069329, filed Mar. 18, 2008 and Japanese application no. 2008-187206, filed Jul. 18, 2008, each of which is incorporated by reference in its entirety.

TECHNICAL FIELD

The present invention relates to flocculent yeast belonging to *Kluyveromyces marxianus* which flocculation property has been enhanced for bioethanol production, and a method for producing the same, etc.

BACKGROUND ART

Microorganisms play a critical role for producing industrial products. Thus, it has been an object to conduct production more efficiently and at a lower cost. These methods of solving this object were to select a strain showing a higher productivity, and to examine the culture conditions such as medium composition for culturing microorganisms, culture temperature, etc. Under recent development of molecular genetics, as one alternative for such strain, a technique of specifying an excellent gene from a conventional strain, and utilizing the gene for transforming a strain can be exemplified. Conventionally, in yeasts that have been used to produce useful foods, transformation has been widely performed to achieve more effective production.

As one transformation to achieve effective production, a transformation for enhancing flocculation property of the cells can be exemplified. Alcohol production by fermentation method is conducted by the use of a technique of a batch fermentation or continuous fermentation, using a strain having a particularly high alcohol productivity among *Saccharomyces cerevisiae*, which is a fermentation yeast. Conventional batch fermentation method comprises adding molasses etc. to alcohol fermentation yeast as raw material, and culturing it under a certain condition to generate alcohol. The generated alcohol is recovered by distillation by heating the culture solution. However, yeasts remaining in the culture solution are killed by heating. Therefore, it is necessary to supplement yeast solution to continue alcohol production. Such process is inefficient and involves a high cost. When flocculent yeasts are used, it is possible to recover alcohol in the supernatant while allowing the solution to stand still and to add a new fermentation solution to the precipitated flocculent yeast to conduct again the alcohol production. Therefore, flocculent yeasts were awaited in the alcohol production by batch fermentation.

As a technique of transformation to confer flocculation property, the following can be exemplified:
A practical flocculent alcohol-fermenting yeast produced by introducing a flocculation gene expression cassette which is a foreign DNA into any marker gene region on the chromosome of alcohol-fermenting yeast, and a method of breeding the same (Patent Document 1); a method for producing yeast having an enhanced flocculation property comprising obtaining a DNA encoding a protein domain associated with the flocculation property of the flocculation gene of yeast, and introducing the DNA into beer yeast (Patent Document 2); and establishment of flocculent yeast for fuel ethanol production (Nonpatent Document 1). These transformed yeasts that have been already reported are produced by introducing flocculation gene derived from *Saccharomyces cerevisiae* into alcohol-producing yeast belonging to *Saccharomyces cerevisiae*. On the other hand, transformed yeast wherein flocculation gene derived from *Saccharomyces cerevisiae* has been introduced into yeast belonging to a genus other than *Saccharomyces cerevisiae* has not been reported so far, and it was not known at all whether flocculation gene derived from *Saccharomyces cerevisiae* is associated with the control of flocculation property in yeast other than *Saccharomyces cerevisiae* or not.

The whole genome has been analyzed in *Saccharomyces cerevisiae*, and the flocculation genes have been specified. The set of FLO genes associated with flocculation property include FLO1 gene present on the $1^{st}$ chromosome (Nonpatent document 2); FLO5 gene present on the $8^{th}$ chromosome (Nonpatent document 3); FLO8 gene present on the $5^{th}$ chromosome (Nonpatent document 4); FLO9 gene present on the $1^{st}$ chromosome (Nonpatent document 5); FLO10 gene present on the $11^{th}$ chromosome (Nonpatent document 6), etc. These genes are considered to be lectin-like proteins having a nucleotide sequence similar to FLO1.

Presently, from the viewpoint of petroleum supply, energy sources are searched at a global level among biological resource (biomass), as an alternative to petroleum. As one of new energies by biomass, there exists bioethanol, which is a biomass fuel. In bioethanol, botanical resources containing a large amount of carbohydrate or starch are utilized. As a method for producing alcohol by microorganism using biomass as raw material, a fermentation production method of ethanol with *Saccharomyces cerevisiae* comprising saccharizing ground materials of Sago Palm raw wood (Patent Document 3), and a method of producing alcohol for fuel from waste such as garbage by using yeast belonging to *Saccharomyces cerevisiae* (Patent Document 4) are disclosed. Yeasts having a thermotolerance that can meet biomass treatment and having a high flocculation property similarly as alcohol-producing yeast are awaited to utilize in bioethanol production.

Yeast *Kluyveromyces marxianus* is a yeast having thermotolerance, and expression of enzyme alcohol dehydrogenase (Adh) associated with the conversion from sugar to ethanol has been confirmed by Lertwattanasakul and Yamada et al. (Nonpatent Document 7). *Kluyveromyces marxianus* can not only produce ethanol but as it has a high protein productivity it is considered to be very useful in the industrial production. However as a method for transforming *Kluyveromyces marxianus* is not generally established, studies are not progressing so far. Therefore, *Kluyveromyces marxianus* transformant strain suitable for industrial production of bioethanol has not at all been reported so far.

Patent Document 1: Japanese Patent No. 3040959
Patent Document 2: Japanese Patent No. 3643404
Patent Document 3: Japanese Laid-Open Patent Application No. 2007-195406
Patent Document 4: Japanese Laid-Open Patent Application No. 2006-325577
Nonpatent Document 1: Biotechnol Lett, 30:97-102, 2008
Nonpatent Document 2: Yeast, 9:423-427, 1993
Nonpatent Document 3: Science, 265:2077-2082, 1994
Nonpatent Document 4: Nature 387:78-81, 1997
Nonpatent Document 5: Proc. Natl. Acad. Sci. U.S.A. 92: 3809-3813, 1995
Nonpatent Document 6: Nature 369: 371-378, 1994
Nonpatent Document 7: Biosci. Biotechnol. Biochem. 71:1170-82, 2007

DISCLOSURE OF THE INVENTION

Object to be Solved by the Invention

The object of the present invention is to provide a novel *Kluyveromyces marxianus* transformant having thermotolerance and flocculation property suitable for industrial production of bioethanol by introducing a foreign flocculation gene into *Kluyveromyces marxianus*, and to provide an efficient method for producing the above transformant.

Means to Solve the Object

The present inventors focused on the flocculation gene FLO of *Saccharomyces cerevisiae* as a foreign gene to confer flocculation property to *Kluyveromyces marxianus*, and produced a straight-chain (linear) DNA fragment comprising a known expression promoter sequence and a FLO gene sequence derived from *Saccharomyces cerevisiae*, as a FLO gene expression cassette to induce FLO gene expression. As a result of introducing this linear DNA fragment into *Kluyveromyces marxianus*, the present inventors have confirmed that *Kluyveromyces marxianus* transformant can be obtained efficiently, and unexpectedly the flocculation property of the above transformant is significantly enhanced. The present invention has been thus completed.

Specifically, the present invention relates to:

[1] a method for producing a *Kluyveromyces marxianus* transformant having a flocculation property and thermotolerance comprising the following steps (A) to (C) sequentially:
(A) a step of producing *Saccharomyces cerevisiae* transformant by introducing a marker gene sequence and an expression promoter sequence in the upstream of an endogenous FLO gene of *Saccharomyces cerevisiae*;
(B) a step of obtaining a DNA fragment containing the marker gene sequence, the expression promoter sequence, and a FLO gene sequence, from a chromosomal DNA derived from the *Saccharomyces cerevisiae* transformant produced in step (A); and
(C) a step of producing a *Kluyveromyces marxianus* transformant by introducing the DNA fragment obtained in step (B) into *Kluyveromyces marxianus* as a FLO gene expression cassette;

[2] the method for producing a *Kluyveromyces marxianus* transformant according to [1], wherein the endogenous FLO gene of *Saccharomyces cerevisiae* is at least one FLO gene selected from FLO1 gene, FLO5 gene, FLO9 gene and FLO10 gene;

[3] the method for producing a *Kluyveromyces marxianus* transformant according to [1] or [2], wherein the marker gene is an auxotrophic marker gene;

[4] the method for producing a *Kluyveromyces marxianus* transformant according to any one of [1] to [3], wherein the auxotrophic marker gene is at least one auxotrophic gene related to a production of histidine, leucine, uracil, methionine, lysine, adenine, tryptophan or arginine;

[5] the method for producing a *Kluyveromyces marxianus* transformant according to [4], wherein the auxotrophic marker gene is URA3 gene;

[6] the production method according to any one of [1] to [5], wherein the *Kluyveromyces marxianus* is a *Kluyveromyces marxianus* mutant having a mutation in at least one auxotrophic gene related to a production of histidine, leucine, uracil, methionine, lysine, adenine, tryptophan or arginine;

[7] the method for producing a *Kluyveromyces marxianus* transformant according to any one of [1] to [6], wherein the expression promoter is glyceraldehyde-3-phosphate dehydrogenase3 (TDH3) promoter;

[8] the method for producing a *Kluyveromyces marxianus* transformant according to any one of [1] to [7], comprising introducing a linear DNA fragment into *Kluyveromyces marxianus* as a FLO gene expression cassette;

[9] the method for producing a *Kluyveromyces marxianus* transformant according to any one of [1] to [8], wherein the *Kluyveromyces marxianus* transformant is RAK4299 strain (NITE BP-514), RAK4300 strain (NITE BP-515), RAK4301 strain (NITE BP-516) or RAK4302 strain (NITE BP-517).

Further, the present invention relates to:

[10] a *Kluyveromyces marxianus* transformant having a flocculation property and thermotolerance produced by the production method according to any one of [1] to [8]; and

[11] the *Kluyveromyces marxianus* transformant according to [10] which is RAK4299 strain (NITE BP-514), RAK4300 strain (NITE BP-515), RAK4301 strain (NITE BP-516) or RAK4302 strain (NITE BP-517).

Effect of the Invention

According to the present invention, it is possible to produce yeasts having excellent flocculation property and thermotolerance by transforming *Kluyveromyces marxianus*, and to provide effective yeasts for the industrial production of bioethanol.

Figure 1:
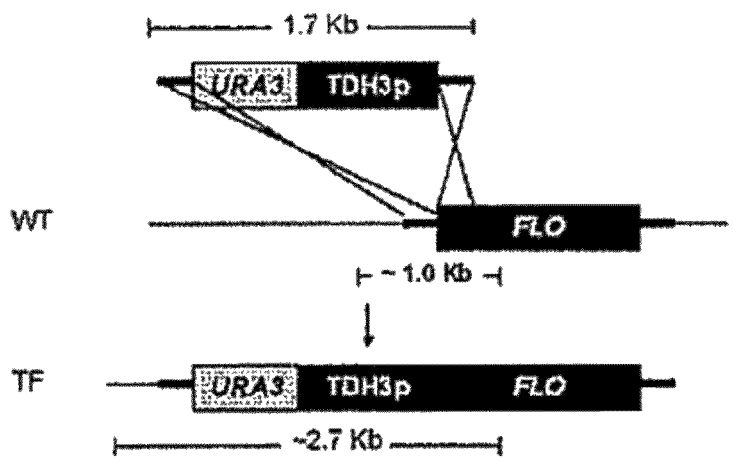
FIG. 1
It is a chart showing the introduction of TDH3 promoter and URA3 DNA fragment derived from pST106 plasmid in the upstream of FLO gene.

It is a figure showing the DTT effect in the transformation efficiency of *Kluyveromyces marxianus* DMKU3-1042.

FIG. 12

It is a figure showing the effect of the DNA fragment size in the transformation efficiency of *Kluyveromyces marxianus* DMKU3-1042.

FIG. 13

It is a figure showing the effect of the temperature and time of the heat shock for the transformation efficiency of *Kluyveromyces marxianus* DMKU3-1042.

FIG. 14

It is a figure showing that *Kluyveromyces marxianus* DMKU3-1042 is the most effective strain in the transformation using a DNA fragment.

BEST MODE OF CARRYING OUT THE INVENTION

The method for producing yeast having flocculation property and thermotolerance of the present invention is not particularly limited as long as it is a method comprising introducing FLO gene expression cassette into a thermotolerant yeast *Kluyveromyces marxianus*. The above-mentioned FLO gene may be any FLO gene that can confer flocculation property to *Kluyveromyces marxianus*, and for example, FLO gene of *Saccharomyces cerevisiae* which the full-genome sequence is analyzed can be suitably exemplified. More specifically, FLO1 gene, FLO5 gene, FLO9 gene, FLO10 gene, etc. of *Saccharomyces cerevisiae* can be suitably exemplified. Concerning the FLO gene information of *Saccharomyces cerevisiae*, the nucleotide sequence information can be obtained from the genome databases of DDBJ (DNA Data Bank of Japan), EMBL-EBI (European Molecular Biology Laboratory), GenBank-NCBI (National Center for Biotechnology Information), SGD (*Saccharomyces* Genome Database), etc.

The above-mentioned FLO gene expression cassette is not particularly limited as long as it can induce the expression of FLO gene in *Kluyveromyces marxianus*, while a FLO gene expression cassette containing a marker gene sequence to select efficiently the transformant, and which is designed so that the FLO gene expression is controlled by the expression promoter is preferred. Examples of the above-mentioned selective marker gene include genes that are resistant to drugs such as antibiotics, genes encoding a deleted product in the recipient (host) cell such as auxotrophic marker gene, etc. Further, examples of drug-resistant genes include genes resistant to drugs such as ampicillin, bleomycin, kanamycin, oligomycin, etc. and examples of auxotrophic maker genes include HIS3, URA3, LEU2, etc. Particularly, it is preferred to use an auxotrophic marker gene. By combining an auxotrophic marker gene and a selective medium, it is possible to select a cell expressing a marker gene, and for example, when an auxotrophic gene of URA3 is introduced into a cell, the transformed host cell can be grown in a medium free of uracil, and it will be possible to select a strain conferred with flocculation property. The above-mentioned expression promoter is not particularly limited, and specific examples include glyceraldehyde-3-phosphate dehydrogenase3 (TDH3, GAP) promoter, TDH1 promoter, TDH2 promoter, PHO5 promoter, PGK promoter, ADH promoter, GAL1 promoter, GAL10 promoter, heat shock protein promoter, MFα1 promoter, CUP1 promoter, etc. These promoter sequences may be a genomic DNA sequence derived from an organism, or a DNA sequence obtained artificially by a chemical technique, etc.

It is preferred to use a mutant of *Kluyveromyces marxianus* wherein the gene to be the marker is mutated to perform transformation by introducing a FLO gene expression cassette. The method for obtaining a mutated gene is not particularly limited, and a conventionally known method can be used. As a method by UV irradiation, for example, a method of Hashimoto et al. (Applied and Environmental Microbiology, 71(1): 312-319, 2005) can be exemplified. In this method, UV is irradiated for 20 seconds from a distance of 35 cm to a yeast strain grown on a plate to obtain 0.05 to 0.2% mutant. According to this method, auxotrophic mutants of histidine (His), leucine (Leu), arginine (Arg), uracil (Ura), methionine (Met) and tryptophan (Trp) can be obtained. Alternatively, there is a method comprising introducing a DNA having a nucleotide sequence homologous to the target gene, such as gene disruption cassette vector, etc., and that cannot function as a gene, into a cell, to induce homologous recombination and to inactivate the gene (Japanese Laid-Open Patent Application No. 2001-46053). In case of mutating a gene which expression cannot be confirmed visually, it is necessary to introduce a marker gene that can be observed by cell drug (antibiotics, etc.) sensitivity test, cell growth rate, enzyme activity test, optical means or auxotrophic test.

As a method for producing yeast of the present invention using a FLO gene expression cassette as stated above comprising an auxotrophic marker gene sequence and a FLO gene sequence derived from *Saccharomyces cerevisiae*, and which expression cassette is designed so that the expression of the FLO gene is controlled by the expression promoter, a production method comprising sequentially the following steps (A) to (C) can be exemplified:

(A) a step of producing *Saccharomyces cerevisiae* transformant by introducing an auxotrophic marker gene sequence and an expression promoter sequence in the upstream of an endogenous FLO gene of *Saccharomyces cerevisiae*;

(B) a step of obtaining a DNA fragment containing the auxotrophic marker gene sequence, the expression promoter sequence, and a FLO gene sequence, from a chromosomal DNA derived from the *Saccharomyces cerevisiae* transformant produced in step (A); and (C) a step of producing a *Kluyveromyces marxianus* transformant by introducing the DNA fragment obtained in step (B) into *Kluyveromyces marxianus* mutant having a mutation in the auxotrophic gene corresponding to auxotrophic marker gene contained in the DNA fragment, as a FLO gene expression cassette.

In the above step (A), the *Saccharomyces cerevisiae* transformant can be produced by introducing a DNA fragment for transformation comprising an auxotrophic marker gene sequence and a FLO gene sequence derived from *Saccharomyces cerevisiae* into a *Saccharomyces cerevisiae* strain in which auxotrophic gene has been mutated. As the *Saccharomyces cerevisiae* strain in which the auxotrophic gene has been mutated, commercially available strains such as *Saccharomyces cerevisiae* BY4700 strain in which uracil auxotrophic gene has been mutated; *Saccharomyces cerevisiae* BY4740 strain in which auxotrophic genes related to the production of uracil, leucine and lysine have been mutated; *Saccharomyces cerevisiae* BY4743 strain in which auxotrophic genes related to the production of histidine, leucine and uracil have been mutated; *Kluyveromyces marxianus* RAK3605 with a uracil auxotrophic gene mutation produced according to the method of Hashimoto et al. (Applied and Environmental Microbiology, 71(1):312-319, 2005), etc. can be used. Further, in the production of the above-mentioned DNA fragment for transformation, a DNA fragment consisting of the sequence from the initiation codon ATG to the 40$^{th}$ nucleotide (base) including ATG can be used according to the sequence information of *Saccharomyces cerevisiae* FLO gene. For example, examples of the nucleotide sequence of the DNA fragment consisting of 40 nucleotides are: atgacaatgcctcatcgctatatgttttggcagtcttta (SEQ ID No: 1) when derived from FLO1 gene, atgacaattgcacaccactgcatattttggtaatcttgg (SEQ ID No: 2) when derived from FLO5 gene, atgtctctggcacattattgtttactactagccatcgtca (SEQ ID No: 3) when derived from FLO9 gene, and atgcctgtggctgctc-gatatatattttgaccggcctat (SEQ ID No: 4) when derived from FLO10 gene, etc. By annealing the DNA fragment produced based on the nucleotide sequence information of these FLO genes, introducing the same into a plasmid having an expression promoter sequence and an auxotrophic marker gene sequence, and amplifying the intended domain by PCR, the DNA sequence for FLO gene expression cassette can be obtained. The above-mentioned plasmid having an expression promoter sequence and an auxotrophic marker gene sequence is not particularly limited, and preferred examples include plasmid URA3-TDH3p having TDH3p as an expression promoter, and uracil auxotrophic gene as auxotrophic gene (hereinafter referred to as "pST106"), produced according to the method of Turgeon et al. (Plasmid 51:24-36, 2004).

As a method for introducing a DNA fragment for transformation into a gene mutant strain, a general transformation technique for introducing a DNA fragment can be used. For example, any of the conjugation method, electroporation method, competent cell method, microinjection method, and particle gun method, etc. can be used. Further, a DNA fragment for transformation can be introduced by performing heat shock in a medium containing alkali metal ion and polyethylene glycol according to the method of Akada et al. (Japanese Laid-Open Patent Application No. 2005-269920).

In the above step (A), examples of *Saccharomyces cerevisiae* transformant produced by using *Saccharomyces cerevisiae* BY4700 strain in which uracil auxotrophic gene has been mutated include the transformants produced in the following Examples, such as *Saccharomyces cerevisiae* RAK3977 strain introduced with URA3-TDH3p-FLO401, *Saccharomyces cerevisiae* RAK3979 strain introduced with URA3-TDH3p-FLO405, *Saccharomyces cerevisiae* RAK3981 strain introduced with URA3-TDH3p-FLO409, *Saccharomyces cerevisiae* RAK3983 strain introduced with URA3-TDH3p-FLO4010, etc.

In the above step (B), examples of a method for obtaining a DNA fragment encoding FLO gene expression cassette from the chromosomal DNA derived from *Saccharomyces cerevisiae* transformant produced in step (A) include a method comprising purifying the chromosomal DNA of the *Saccharomyces cerevisiae* transformant by operations including dissolution, stirring, extraction and centrifugation by usual method using SDS (sodium lauryl sulfate) solution, etc., and performing PCR reaction using the purified chromosomal DNA as a template. At the time of the PCR reaction, by using a primer designed to amplify the DNA sequence containing the FLO gene expression cassette sequence comprising an auxotrophic marker gene sequence, expression promoter sequence, and FLO gene sequence, a DNA fragment encoding a FLO gene expression cassette can be obtained.

In the above step (C), any *Kluyveromyces marxianus* mutant in which any auxotrophic gene has been mutated can be used as long as it is a *Kluyveromyces marxianus* auxotrophic mutant having a mutation in the chromosomal gene corresponding to the auxotrophic marker gene contained in the FLO gene expression cassette can be used, and a *Kluyveromyces marxianus* mutant in which auxotrophic genes for histidine, leucine, uracil, methionine, lysine, adenine, tryptophan, arginine, etc. have been mutated can be selected. For example, as it is shown in the following Examples, when using a URA3-TDH3p-FLO gene fragment as a FLO gene expression cassette, it can be produced by using *Kluyveromyces marxianus* RAK3605 strain of *Kluyveromyces marxianus* strain in which uracil auxotrophic gene has been mutated.

Yeasts having flocculation property and thermotolerance produced using the production method of the present invention are not particularly limited, and specific examples include *Kluyveromyces marxianus* RAK4299 strain (accession no. NITE BP-514) in which FLO gene expression cassette (URA3-TDH3p-FLO1) derived from *Saccharomyces cerevisiae* RAK3977 strain has been introduced into *Kluyveromyces marxianus* RAK3605 strain in which uracil auxotrophic gene has been mutated; *Kluyveromyces marxianus* RAK4300 strain (accession no. NITE BP-515) in which FLO gene expression cassette (URA3-TDH3p-FLO5) derived from *Saccharomyces cerevisiae* RAK3979 strain has been introduced into *Kluyveromyces marxianus* RAK3605 strain in which uracil auxotrophic gene has been mutated; *Kluyveromyces marxianus* RAK4301 strain (accession no. NITE BP-516) in which FLO gene expression cassette (URA3-TDH3p-FLO9) derived from *Saccharomyces cerevisiae* RAK3981 strain has been introduced; *Kluyveromyces marxianus* RAK4302 strain (accession no. NITE BP-517) in which FLO gene expression cassette (URA3-TDH3p-FLO10) derived from *Saccharomyces cerevisiae* RAK3983 strain has been introduced into *Kluyveromyces marxianus* RAK3605 strain in which uracil auxotrophic gene has been mutated, etc. The above-mentioned four *Kluyveromyces marxianus* mutants are deposited to National Institute of Technology and Evaluation, Patent Microorganisms Depositary (address: 2-5-8 Kazusakamatari, Kisarazu-shi, Chiba).

In the present invention, a medium for selecting the transformed strain may be a medium for culturing yeast that is generally used, and YPD medium (1% yeast extract, 2% peptone, 2% glucose) and YM medium (0.3% yeast extract, 0.3% malt extract, 0.5% peptone, 1% glucose) that have been referred in the Examples can be used. The types of the carbon source and nitrogen source of the medium, or additives to medium such as alkali metal ion, etc. are not limited as long as it is a medium on which the transformants can be effectively selected. The culture is performed at 25° C. to 33° C., preferably 28° C. to 30° C., for 1 to 5 days, preferably 2 to 3 days.

In the following, the Examples are described in order to further explain the present invention, while the present invention is not limited to these.

Example 1

Insertion of Overexpression Promoter TDH3p in the Upstream of FLO Gene of *Saccharomyces cerevisiae*

A. Amplification of URA3-TDH3p Fragment

Figure 2:
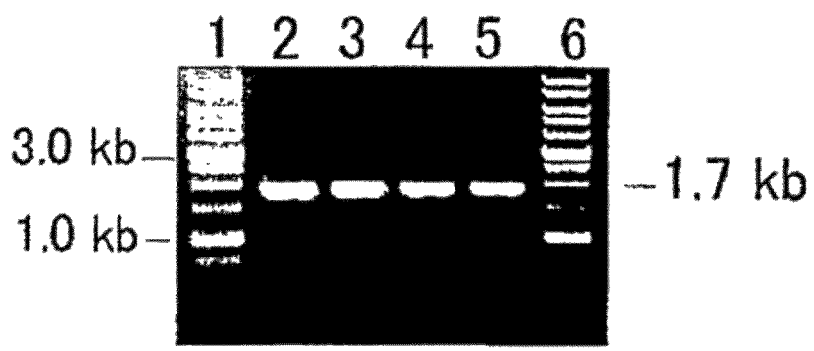
FIG. 2
It is a figure showing the electrophoresis results of DNA fragment for transformation. (Lane 1, 6: DNA ladder, lane 2: derived from FLO3; lane 3: derived from FLO5; lane 4: derived from FLO9; lane 5: derived from FLO10)

A DNA fragment for transforming *Saccharomyces cerevisiae* has been produced by using pST106 plasmid having URA3 gene sequence being a marker gene, and TDH3 being an expression promoter sequence as a template, and performing PCR reaction using primers shown in Table 1. The above-mentioned primers are designed so as to clip the URA3-TDH3p sequence of pST106 plasmid, and to include 40 nucleotides in the upstream sequence of *Saccharomyces cerevisiae* FLO1, FLO5, FLO9 or FLO 10 gene, respectively. As a PCR reaction solution, a total solution of 10 μl containing a pair of 0.2 μl each of 0.2 μM primers, 1.0 μl of KOD plus buffer (TOYOBO), 1.0 μl of 0.2 mM dNTPs, 0.8 μl of 0.2 mM $MgSO_4$ (TOYOBO), 0.4 μl of 0.4 ng/μl pST106 plasmid, and 0.2 μl of KOD Plus DNA polymerase (TOYOBO), and 6.2 μl of sterile water was used. The reaction was performed as follows: initial heating at 94° C. for 1 minute, followed by 30 cycles of heat denaturation at 94° C. for 20 seconds, annealing at 55° C. for 30 seconds, and elongation reaction at 68° C. for 3 minutes. As a result, DNA fragments, URA3-TDH3p-FLO401, URA3-TDH3p-FLO405, URA3-TDH3p-FLO409 and URA3-TDH3p-FLO4010 (hereinafter these DNA fragments may be referred to as URA3-TDH3p-FLO40s as a whole) each having a homologous sequence of the upstream of FLO1, FLO5, FLO9 or FLO10, respectively were obtained (FIGS. 1 & 2).

TABLE 1

| DNA fragment for transformation to produce (URA3-TDH3p-FLO4Os) | Primer I | | Primer II | |
|---|---|---|---|---|
| URA3-TDH3p-FLO401 | FLO1-401 tattttaattcttgtcaccagtaa acagaacatccaaaaggcgcgcccg | (SEQ ID No: 5) | FLO1-402 taaagactgccaaaaacatatagcg atgaggcattgtcattttatgtgat | (SEQ ID No: 6) |
| URA3-TDH3p-FLO405 | FLO5-401 caaatgattttctttaaattgatta gcaccactaaaaaaaggcgcgcccg | (SEQ ID No: 7) | FLO5-402 ccaagattaccaaaaatatgcagtg gtgtgcaattgtcattttatgtgat | (SEQ ID No: 8) |
| URA3-TDH3p-FLO409 | FLO9-401 gcaatttaaaaagaacaattgtaca ataaaagccccaaaaggcgcgcccg | (SEQ ID No: 9) | FLO9-402 tgacgatggctagtagtaaacaata atgtgccagagacattttatgtgat | (SEQ ID No: 10) |
| URA3-TDH3p-FLO4010 | FLO10-401 tttgttttagggtgcttaatcaaag aacaacaaataaaaaggcgcgcccg | (SEQ ID No: 11) | FLO10-402 ataggccggtcaaaaatatatcg agcagccacaggcattttatgtgat | (SEQ ID No: 12) |

B. Introduction of URA3-TDH3p Sequence into *Saccharomyces cerevisiae*

*Saccharomyces cerevisiae* BY4700 strain was inoculated in a test tube containing 2 ml of YPD medium (1% yeast extract, 2% polypeptone, 2% glucose) and was cultured at 28° C. at 150 rpm overnight. 1 ml of the culture solution was transferred to a petri dish containing 9 ml of YPD medium, and cultured at 28° C. at 150 rpm for 5 hours. The culture solution was centrifuged at 8500 rpm for 3 minutes, and the cells were collected and washed once with sterilized distilled water. The residues were dissolved with 100 μl of sterilized distilled water. The transformation solution was prepared by mixing 115 μl of 60% PEG3350, 5 μl of 4M lithium acetate and 15 μl of distilled water. 50 μl of cell lysate was transferred to a microcentrifugation tube containing 135 μl of transformation buffer, added with 10 μl of salmon DNA and 5 μl of each of the four DNA fragments (URA3-TDH3p-FLO4s) prepared in the above A, and the mixture was stirred well by using a stirrer for 30 seconds. The tube was subjected to heat treatment at 42° C. for 40 minutes. 200 μl of the transformed cell lysate was spread on the selective medium, and cultured at 28° C. for 2 to 3 days. The colony of cells grown on a uracil-lacking medium was collected at random to separate the transformed cells. The transformed cells were grown on YPD medium, and stored at 4° C.

C. Confirmation of *Saccharomyces cerevisiae* Transformant by PCR

1. Preparation of DNA for PCR

The transformed cells produced in the above B were inoculated on a well of a 12 well-plate containing 1 ml of YPD medium, and cultured at 28° C. for 20 hours. After the culture, 1 ml of YPD medium was added and further cultured at 28° C. for 4 hours. 1.5 ml of the culture solution was collected, transferred to a microcentrifugation tube, centrifuged at 12000 rpm for 3 minutes to remove the supernatant, and the residues were washed once with sterilized distilled water. After the distilled water was removed, 7.5 μl of the cells were transferred to a microcentrifugation tube containing 2.5 μl of 1% SDS, and then stirred well by using a stirrer for 30 seconds. The cells were centrifuged at 12000 rpm for 3 minutes to recover the supernatant. The supernatant was used for colony PCR.

2. Colony PCR

Figure 3:
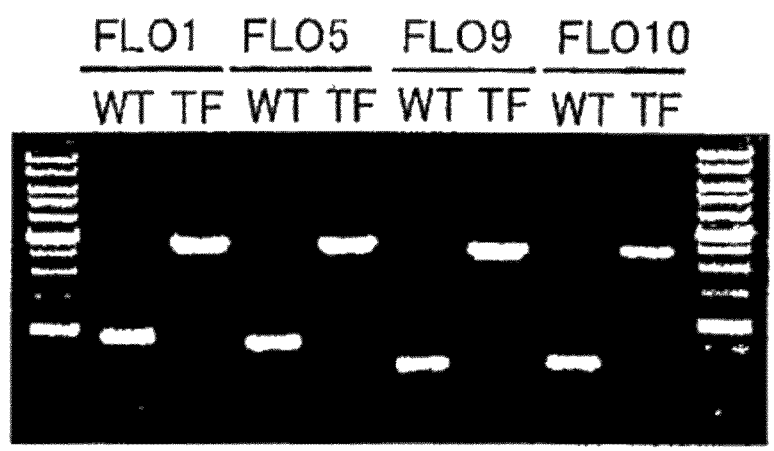
FIG. 3
It is a figure showing the electrophoresis results of the chromosomal DNA of *Saccharomyces cerevisiae* BY4700 introduced with DNA fragment for transformation (TF), and that of the chromosomal DNA without introduction of DNA fragment (WT).

Colony PCR was performed using the primers shown in Table 2. As a PCR reaction solution, a total solution of 10 μl containing a pair of 0.4 μl each of 0.4 μM primers, 1.0 μl of KOD dash buffer (TOYOBO), 1.0 μl of 0.2 mM dNTPs (TOYOBO), 0.2 μl of KOD dash DNA polymerase (TOYOBO), 4.0 μl of sterile water, and 5.0 μl of chromosomal DNA of the transformed cell produced in the above as a template was used to perform PCR. The reaction was performed as follows: initial heating at 94° C. for 1 minute, followed by 30 cycles of heat denaturation at 94° C. for 20 seconds, annealing at 60° C. for 2 seconds, and elongation reaction at 74° C. for 4 minutes. As a result, it has been confirmed that transformants in which URA3-TDH3p-FLO4Os have been introduced into *Saccharomyces cerevisiae* BY 4700 strain have been produced, as shown in FIG. 3. Four types of *Saccharomyces cerevisiae* transformants thus produced contain URA3 gene sequence which is a selective marker and TDH3 promoter sequence in the upstream of endogenous FLO1, FLO5, FLO9, or FLO10 gene.

TABLE 2

| Template | Primer I | | Primer II | |
|---|---|---|---|---|
| FLO1 TF | FLO1-517 gaattctagccttcctctgctc | (SEQ ID No: 13) | FLO1-5-415c ctagggttacgtttgttggggt | (SEQ ID No: 14) |
| FLO5 TF | FLO5-413 ggcaccctcgagaattacactt | (SEQ ID No: 15) | FLO1/5-415c ctagggttacgtttgttggggt | (SEQ ID No: 14) |
| FLO9 TF | FLO9-362 gtacatcacacacgaccacaga | (SEQ ID No: 16) | FLO9-455c taagaacccgtctgtggtggta | (SEQ ID No: 17) |
| FLO10 TF | FLO10-311 gttgtttggtatgtatccgccg | (SEQ ID No: 18) | FLO10-284c gcacaagtatctgatgcgccat | (SEQ ID No: 19) |

Example 2

Introduction of URA3-TDH3P-FLOs Derived from *Saccharomyces cerevisiae* into *Kluyveromyces marxianus*

A. Amplification of URA3-TDH3p-FLOs

Figure 4:
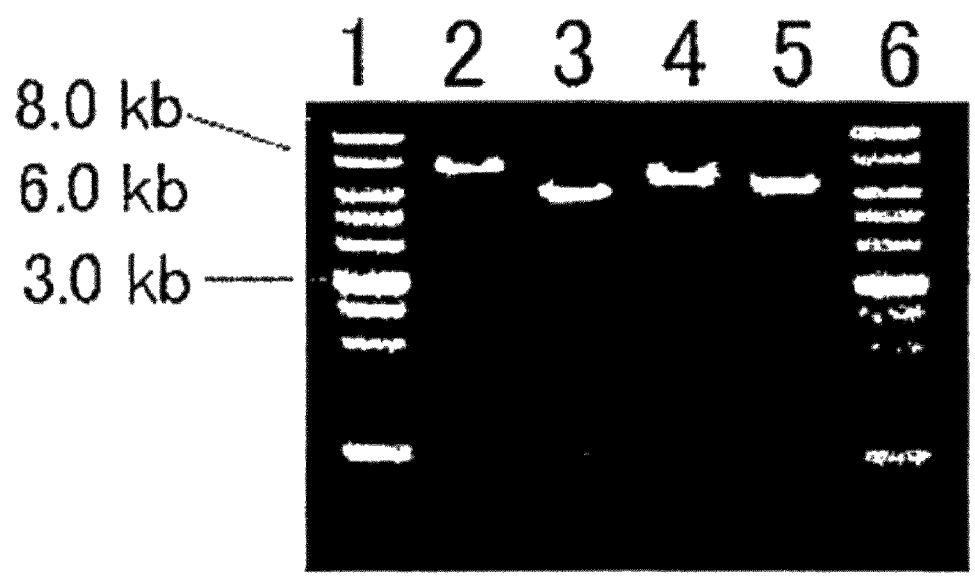
FIG. 4
It is a figure showing the electrophoresis results of four types of recombinant FLO genes of chromosomal DNA of *Saccharomyces cerevisiae* obtained by introducing DNA fragments for transformation (lane 1, 6: DNA ladder, lane 2: URA3-TDH3p-FLO1, lane 3: URA3-TDH3p-FLO5; lane 4: URA3-TDH3p-FLO9, lane 5: URA3-TDH3p-FLO10).

By using a chromosomal DNA derived from *Saccharomyces cerevisiae* transformant produced in Example 1 as a template, a DNA fragment (URA3-TDH3p-FLOs; FLO gene expression cassette) for transforming *Kluyveromyces marxianus* was produced. As it is shown in Table 3, primers for amplifying URA3 sequence, TDH3p sequence and full length FLO gene of each *Saccharomyces cerevisiae* transformant were designed, to amplify DNA fragment URA3-TDH3p-FLOs. The PCR reaction was conducted in the same manner as Example 1A. The reaction was performed as follows: initial heating at 94° C. for 1 minute, followed by 30 cycles of heat denaturation at 94° C. for 20 seconds, annealing at 55° C. for 30 seconds, and elongation reaction at 68° C. for 5 minutes. Thus amplified PCR products were analyzed by agarose electrophoresis or picture of UV irradiation (FIG. 4).

TABLE 3

| Template Recombinant FLO gene | Template derived strain | Primer I | | Primer II | |
|---|---|---|---|---|---|
| URA3-TDH3p-FLO1 | RAK3977 | FLO1-517 | (SEQ ID NO: 13) | FLO1-5037c | (SEQ ID NO: 20) |
| | | gaattctagccttcctctgctc | | aagttggcgatggttcattaattgc | |
| URA3-TDH3p-FLO5 | RAK3979 | FLO5-413 | (SEQ ID NO: 15) | FLO5-3759c | (SEQ ID NO: 21) |
| | | ggcaccctcgagaattacactt | | gtactgcgtgtggcatgtaagcagc | |
| URA3-TDH3p-FLO9 | RAK3981 | FLO9-362 | (SEQ ID NO: 16) | FLO9-4454c | (SEQ ID NO: 22) |
| | | gtacatcacacacgaccacaga | | actagatcttacgttagtactgctg | |
| URA3-TDH3p-FLO10 | RAK3983 | FLO10-311 | (SEQ ID NO: 18) | FLO10-3980c | (SEQ ID NO: 23) |
| | | gttgtttggtatgtatccgccg | | cgccgggcagtagtaactattgtta | |

B. Production of URA3-Deficient Strain of *Kluyveromyces marxianus*

URA3-deficient strains of *Kluyveromyces marxianus* were obtained according to the method of Hashimoto et al. (Appl Microbiol. Biotechnol., 69: 689-696; 2006). Specifically, yeast strains were spread on YPD plate, irradiated with UV for 60 seconds, cultured at 28° C. overnight, and the plate was replicated on 5-FOA medium prepared according to the method of Akada et al. (Yeast 23, 399-405, 2006) and further cultured for 3 days. The grown colonies were isolated, and after confirming the uracil auxotrophy, the strain which transformation has succeeded was named RAK3605 strain.

C. Introduction of URA3-TDH3p-FLOs into *Kluyveromyces marxianus* Chromosome

*Kluyveromyces marxianus* RAK3605 was inoculated into a 250 ml-triangle flask containing 25 ml-YPD medium, and cultured at 28° C. for 18 hours. 25 ml of the culture solution was transferred to a 50 ml-centrifuging tube. Centrifugation was performed at 8500 rpm for 5 minutes to collect the cells and the supernatant was removed. The transformation solution was made to be 600 μl including 400 μl of 60% PEG3350, 60 μl of 1M DTT, 30 μl of 4M lithium acetate, and 110 μl of distilled water. The cells were dissolved with 500 μl of transformation solution. 100 μl of the cell lysate was transferred to a microcentrifugation tube, 5 μl of DNA fragment prepared in the above was added as FLO gene expression cassette, and the mixture was stirred well using a stirrer for 30 seconds. The tube was subjected to heat treatment at 47° C. for 15 minutes. 100 ml of YPD medium was added to the transformed cell lysate, and from which 200 μl was spread on uracil-lacking medium and cultured at 28° C. for 2 to 3 days. Colonies of the cells grown on a uracil-lacking medium were collected to separate the transformed cells. The transformed cells were grown on YPD medium for 1 to 2 days, and stored at 4° C.

Example 3

Flocculation Property of FLO Gene-Expressing *Kluyveromyces marxianus* and *Saccharomyces cerevisiae*

Figure 5:
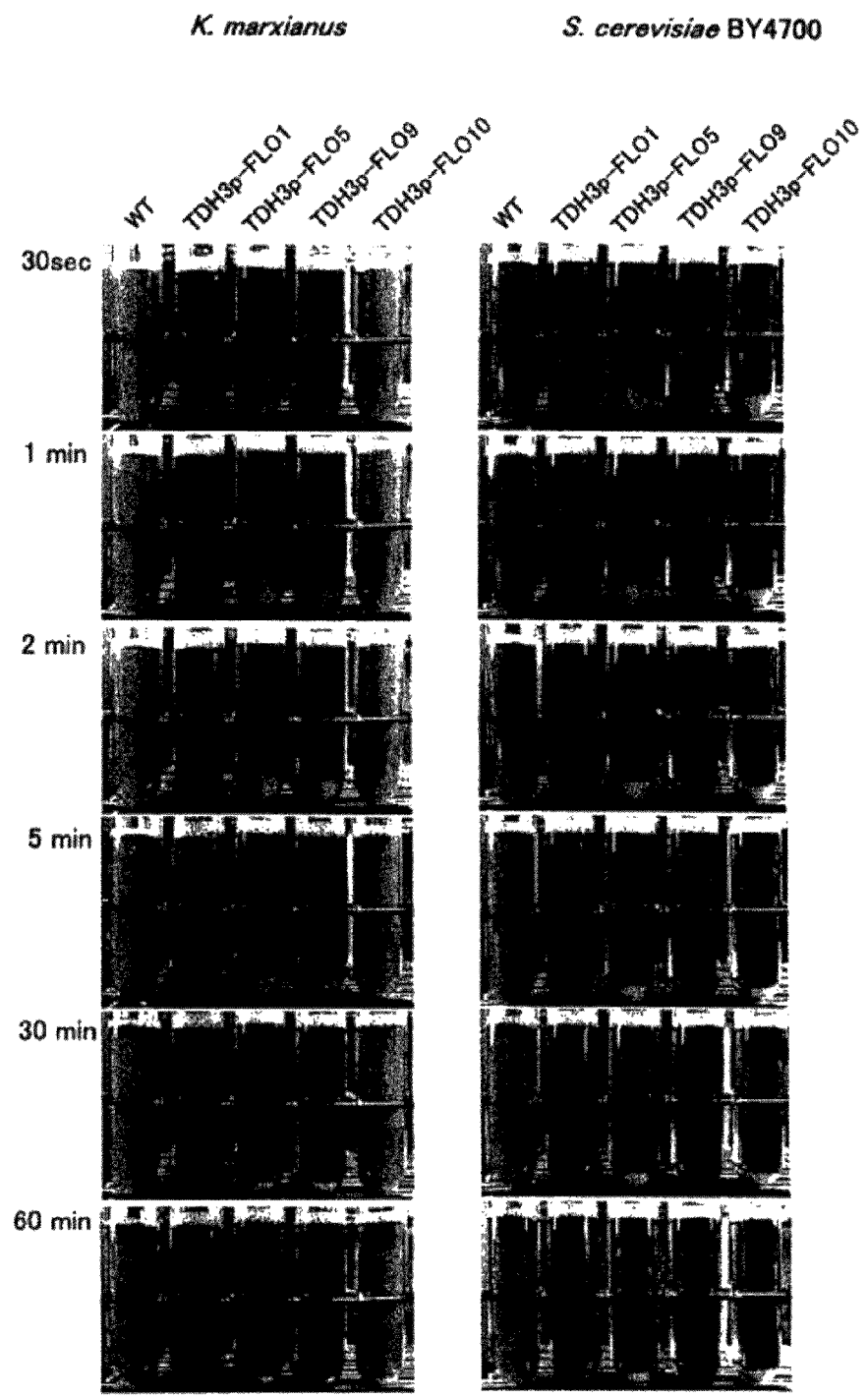
FIG. 5
It is a figure showing the flocculation property of each transformant of *Kluyveromyces marxianus* DMKU3-1042 and *Saccharomyces cerevisiae* BY4700.

FLO gene-expressing *Kluyveromyces marxianus* and *Saccharomyces cerevisiae* were inoculated in a test tube each containing 5 ml of YPD medium, and cultured at 28° C. at 150 rpm for 24 hours. After the culture, the test tubes were stirred well using a stirrer for 15 seconds, which were allowed to stand on a rack for 1 hour, and the flocculating rate was observed over time. As it is shown in FIG. 5, a higher flocculation property was observed in FLO gene-overexpressing strain as compared to the wild-type (WT: *Kluyveromyces marxianus* DMKU3-1042, WT: *Saccharomyces cerevisiae* BY4700).

Example 4

Figure 6:
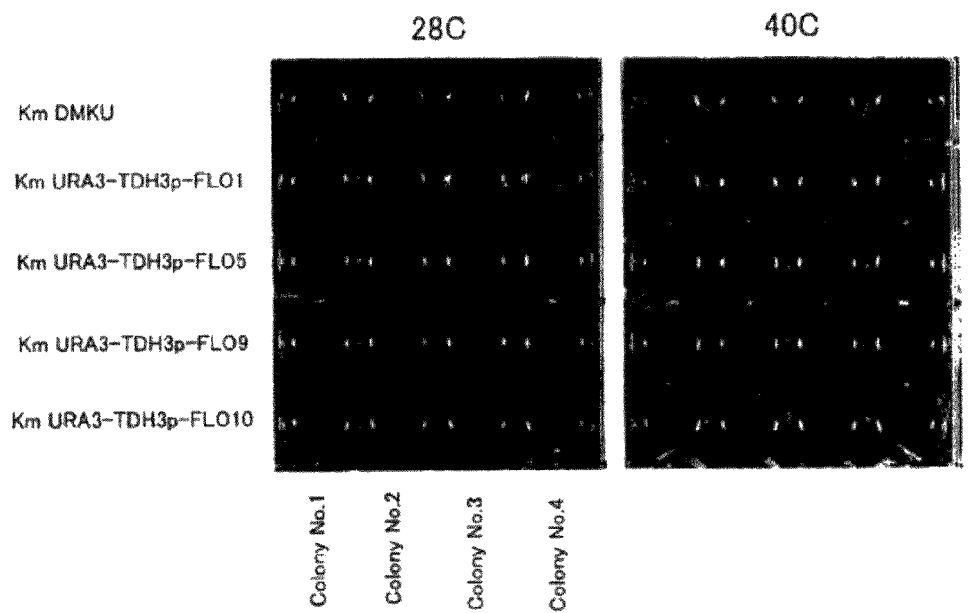
FIG. 6
It is a figure showing the flocculation property of *Kluyveromyces marxianus* transformant at 28° C. and 40° C.
Figure 7:
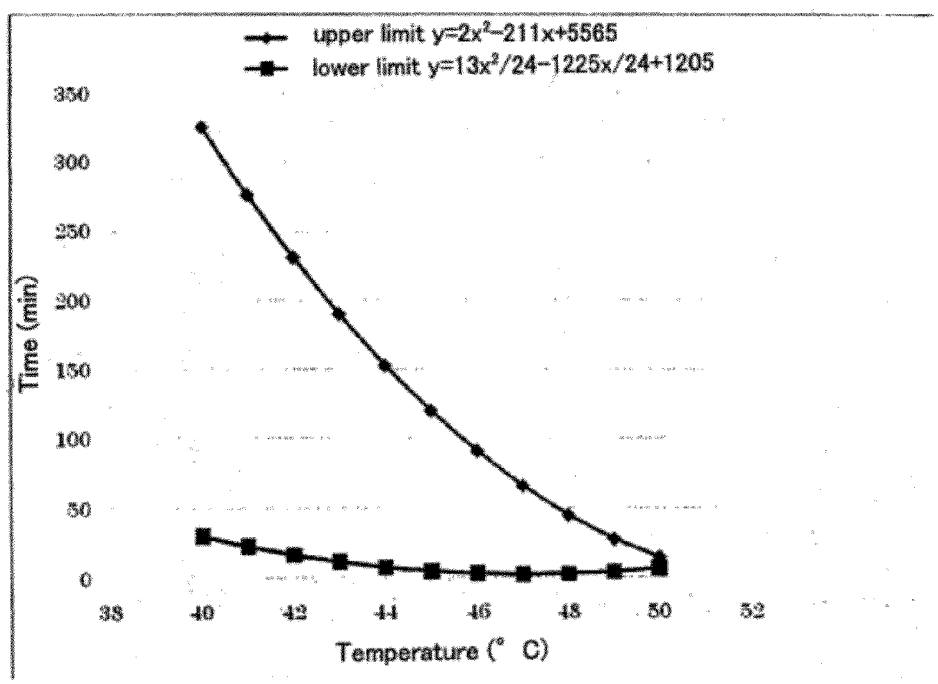
FIG. 7
It is a figure showing the upper limit and lower limit of the reaction time with respect to the temperature for the time of the heat shock at the temperature of 40° C. to 50° C.
Figure 8:
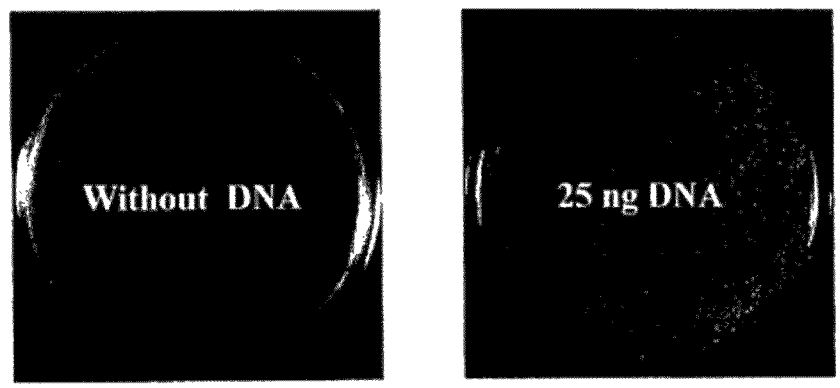
FIG. 8
It is a figure showing the picture of the transformation results of *Kluyveromyces marxianus* DMKU3-1042. By using 25 ng of URA3 fragment of straight-chain DNA, the number of transformants on the plate surface can be obtained.

Flocculation Property of FLO Gene-Overexpressing Strain of *Kluyveromyces marxianus* at High Temperature FLO gene-expressing *Kluyveromyces marxianus* were inoculated into a well of 24-well plate, each well containing 5 ml of YPD medium, and cultured with shaking at 28° C. or 40° C., at 150 rpm for 24 hours. As it is shown in FIG. 6, flocculation property at high temperature was maintained in FLO gene-overexpressing strain of *Kluyveromyces marxianus*.

Reference Example

In the following, results of investigation of conditions in a method for transforming *Kluyveromyces marxianus* effectively by using a straight-chain DNA are shown as a reference example.

[Materials]

1. Medium

As for the YPD medium, 1% yeast extract, 2% peptone, and 2% glucose were dissolved in distilled water and subjected to autoclaving at 121° C. for 20 minutes. The uracil-lacking medium (hereinafter referred to as "−U medium") contained 0.17% yeast derived-nitrogen source (excluding amino acid and ammonium sulfate), 0.5% ammonium sulfate, 2% glucose, and further 0.06% amino acid mixture (4% adenosine sulphate, 16% L-tryptophan, 16% L-histidine hydrochloride, 16% L-methionine, 32% L-leucine, and 16% L-lysine hydrochloride). These ingredients were dissolved in distilled water, and the mixture was adjusted to pH 6.0 with 1N-sodium hydroxide, before subjecting to autoclaving at 121° C. for 20 minutes. In case of a solid medium, 2% agar was added.

2. Yeast Strain

URA3 gene fragments for transformation were obtained from *Saccharomyces cerevisiae* BY4704 (ATCC 200868). As host cells, DMKU3-1042 which is a URA3-lacking strain of *Kluyveromyces marxianus*, NCYC 587 (obtained from National collection of Yeast Cultures, Institute of Food Research, Norwich Research Park, Colney, Norwich, United Kingdom, NR4 7UA); IFO0273 and IFO0277 (those 2 strains were obtained from NITE Biological Resource Center, Department of Biotechnology, National Institute of Technology and Evaluation (NBRC)) were used. All yeasts were cultured on a plate of a fresh YPD medium at 28° C. for 1 to 2 days before being used for transformation.

3. DNA Fragment

URA3 gene fragment derived from *Saccharomyces cerevisiae* BY4704 was amplified using KOD-Plus DNA polymerase (TOYOBO) by PCR. As primer sets, URA3-40 (5'-atcaaagaaggttaatgtggctgtgg-3': SEQ ID No:24) and URA3-40c (5'-ttcgtcattatagaaatcattacgac-3': SEQ ID No:25); URA3-300 (5'-gaagagtattgagaagggcaac-3': SEQ ID No:26) and URA3-300c (5'-tgttgtgaagtcattgacacag-3': SEQ ID No:27); or URA3-1000 (5'-tactaggaaatgagaatttttggaa-3': SEQ ID No:28) and URA3-1000c (5'-tgcgattggcagtggaa-cagtggta-3': SEQ ID No:29) were appropriately used. PCR was performed as follows: heating at 94° C. for 1 minute, followed by 30 cycles of heat denaturation at 94° C. for 20 seconds, annealing at 55° C. for 30 seconds, and elongation reaction at 68° C. for 3 minutes.

[Transformation Method]

*Kluyveromyces marxianus* DMKU3-1042 strain cells, a URA3 gene-deficient strain, were cultured at 28° C. overnight on a petri dish containing YPD medium (1% yeast extract, 2% peptone, 2% glucose, 2% agar), and test cells were collected therefrom. Cells were inoculated into a triangle flask containing 25 ml of YPD liquid medium (1% yeast extract, 2% peptone, 2% glucose) and cultured with shaking at 28° C. for 17 hours, at 150 rpm under aeration. 50 ml of the culture solution was taken, transferred to a centrifugation tube, and centrifuged at 8000 rpm for 2 minutes. The supernatant was removed, and 1.4 ml of transformation buffer (2 ml of 60% PEG3350, 150 µl of 4M lithium acetate, 300 µl of 1M DTT, and 550 µl of sterilized distilled water) was added to the residue, mixed by stirring for 15 seconds, and the mixture solution was transferred to a microcentrifugation tube. Centrifugation was performed at 12000 rpm for 15 seconds, and the supernatant was removed. 500 of the above-mentioned transformation buffer was added to the residue, and stirred well. 100 µl each of the mixture solution were transferred to microcentrifugation tubes, and 25 ng (0.5 µl) of DNA fragment (URA3) was added to the test cells, while it was not added to control. The mixtures were mixed well with a mixer, and performed heat shock at 47° C. for 15 minutes followed by culture. Next, sterile water and 150 µl of −U medium were added to the reaction solutions and suspended. The mixture solutions were spread on a plate of −U solid medium with a spreader, and cultured at 28° C. for 2 to 3 days.

Figure 14:
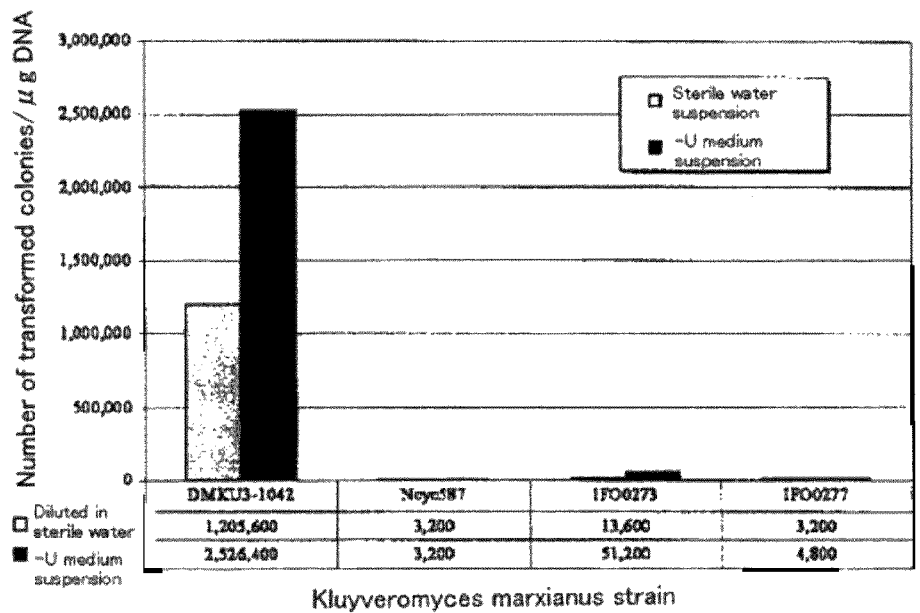

The results of using DNA fragments amplified with URA3-40 (SEQ ID No: 24) and URA3-40c (SEQ ID No: 25) are shown in FIG. 14. With a URA3 gene-deficient strain as a control, strain growth was not observed, while with the test cells, many colonies were observed, demonstrating that DNA of URA3 gene was taken up by the cell.

[Effect of Yeast Cell Concentration]

Figure 9:
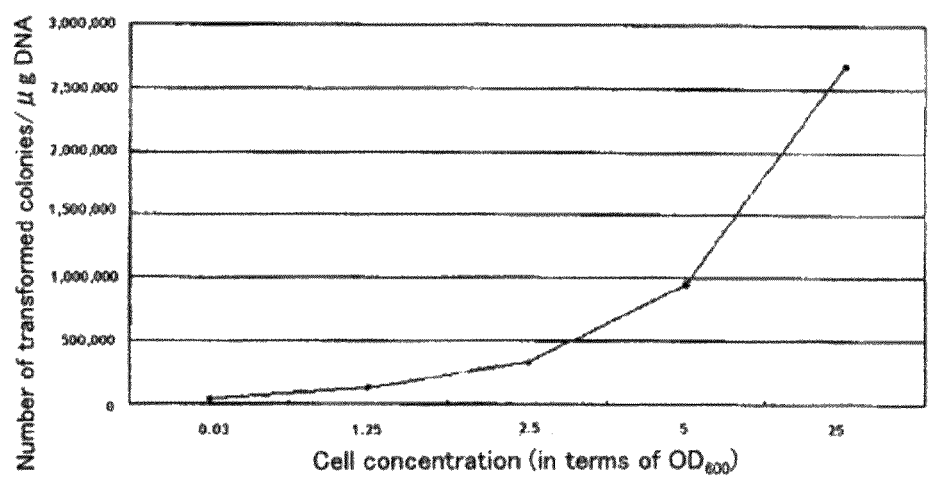
FIG. 9
It is a figure showing the effect of yeast cell concentration in the transformation efficiency of *Kluyveromyces marxianus* DMKU3-1042.

The concentration of the yeast cells grown in YPD liquid medium was measured at an absorbance of 600 nm (OD 600). Transformation was performed under the same conditions as Example 1, except that a heat shock treatment was performed at 42° C. for 2 hours. As a result, as it is shown in FIG. 9, it has been revealed that higher is the concentration of yeast cell, higher is the reactivity.

[Effect of the Composition of the Transformation Solution]

1. Molecular Weight of Polyethylene Glycol (PEG) and Dilution Solvent

Figure 10:
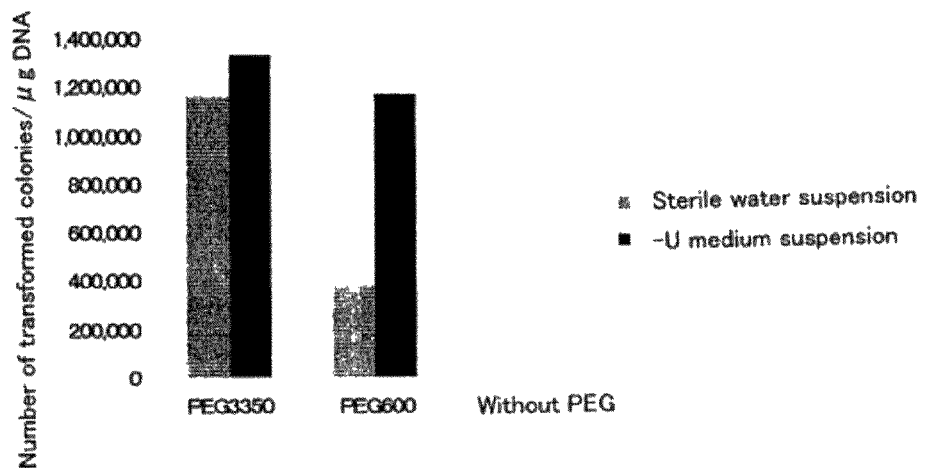
FIG. 10
It is a figure showing the effect of molecular weight of polyethylene glycol (PEG) and diluted solution after heat shock in the transformation efficiency of *Kluyveromyces marxianus* DMKU3-1042.

Under the same conditions as Example 1, the molecular weight of polyethylene glycol (PEG) in the transformation buffer was changed and the transformation was performed. As PEG, PEG3350 (average molecular weight 3350) and PEG600 (average molecular weight 600) were used, and it was adjusted so that the final concentration becomes 40% in the transformation buffer. Further, transformation was performed for control similarly without adding PEG. As it is shown in FIG. 10, effective results were obtained for the case added with PEG3350.

2. DTT

Figure 11:
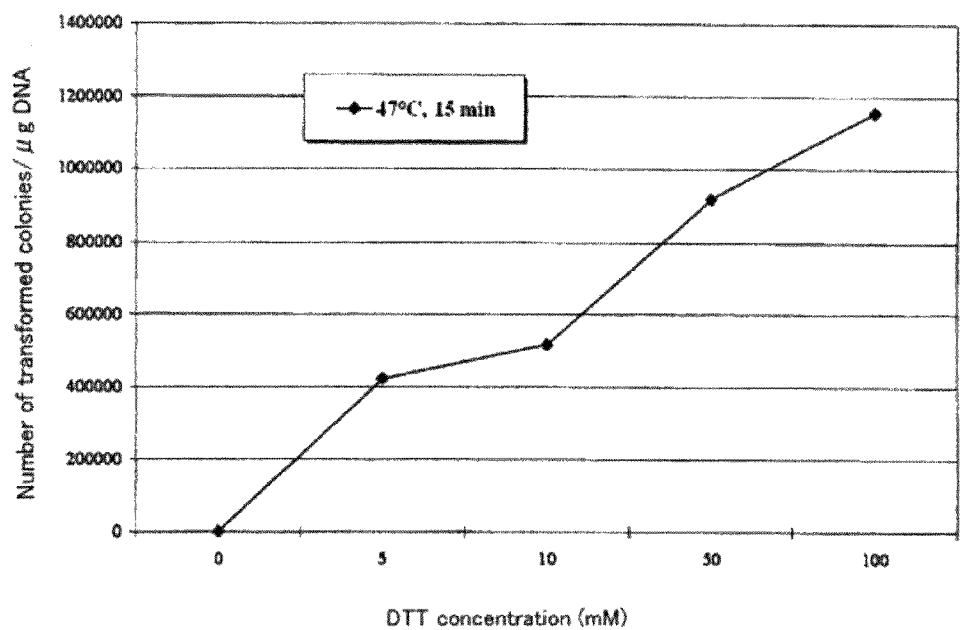
FIG. 11

Under the same conditions as the above-mentioned conditions, transformation was performed by changing the DTT final concentration in the transformation buffer from 0 to 100 mM. As a result, as it is shown in FIG. 11, the DTT effect has been revealed to be concentration dependent.

[Effect of the Size of DNA Fragment Derived From *Saccharomyces cerevisiae* Chromosome]

Figure 12:
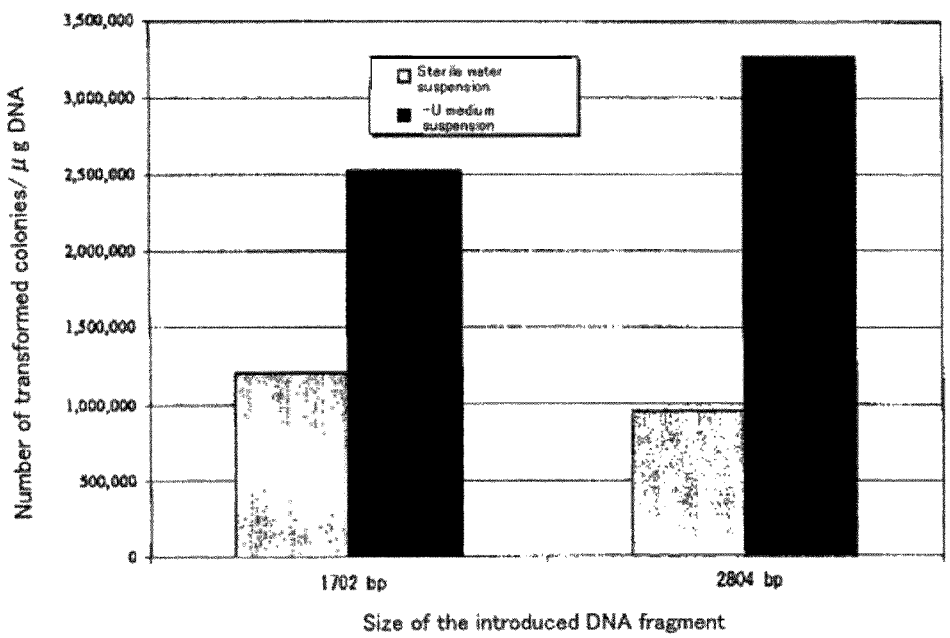

Under the same conditions as the above-mentioned conditions, chromosomal URA3 DNA fragments from *Saccharomyces cerevisiae* were transformed by changing only the amplifying primers. The primer sets of URA3-300 (SEQ ID No:26) and URA3-300c (SEQ ID No:27) so that the DNA size becomes 1.702 kb, or URA3-1000 (SEQ ID No:28) and URA3-1000c (SEQ ID No:29) so that the DNA size becomes 2.804 kb were used for amplification by PCR. As a result, as it is shown in FIG. 12, a high transformation efficiency was shown for both cases of PCR. Suspension of the reaction solution showed a high transformation efficiency when using −U medium.

[Effect of the Time and Temperature of the Heat Shock]

Figure 13:
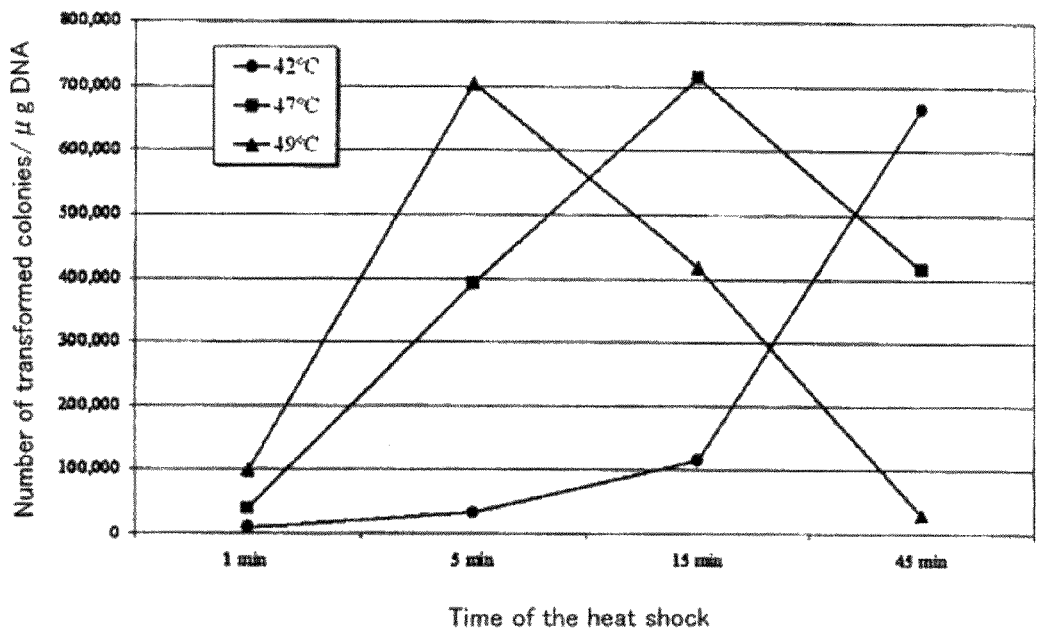

Under the same condition as the above-mentioned conditions, transformation was performed by changing only the temperature and time for the heat shock of the reaction solution after adding a DNA fragment. Heat shock was performed at a temperature of 42° C., 47° C., or 49° C. for 1 minute, 5 minutes, 15 minutes or 45 minutes. As a result, as it is shown in FIG. 13, it has been revealed that the efficient time differs depending on temperature.

[Strain Selection of the Host Cell *Kluyveromyces marxianus*]

Under the same condition as the above-mentioned conditions, transformation was performed by using NCYC587, IF00273, and IF00277 being URA3 gene-deficient strains similarly as *Kluyveromyces marxianus* DMKU3-1042. As a result, as it is shown in FIG. 14, it has been revealed that it was most efficient to use *Kluyveromyces marxianus* DMKU3-1042 as a host cell. Suspension of the reaction solution to −U medium showed a higher transformation efficiency.

The operations in the method for transforming yeast of the present invention are easier as compared to the conventional artificial transformation method, and the time required for transformation is short, showing a high transformation efficiency of $10^6$ or more per 1 μg of DNA. Further, storage of the transformed cells is excellent, and the passage can be sufficiently performed advantageously.

INDUSTRIAL APPLICABILITY

According to the present invention, ethanol-producing yeast having an excellent flocculation property and thermotolerance which is advantageous for the industrial production of bioethanol can be provided.

| | | |
|---|---|---|
| 0-1 | Form PCT/RO/134 (SAFE) | PCT-SAFE |
| 0-1-1 | The indication of the deposited microorganisms or other biological materials (PCT rule 13(2)) has been made by the right mentioned. | Version 3.51.028.203 MT/FOP 20080401/0.20.5.12 |
| 0-2 | International Application Number | |
| 0-3 | Identification Number of the Applicant or Agent | FH19-041 |
| 1 | The indications made below relate to the microorganism or other biological material referred to in the Detailed Description of the Invention. | |
| 1-1 | Paragraph numbers | 0011, 0012, 0024 |
| 1-3 | IDENTIFICATION OF DEPOSIT | |
| 1-3-1 | Name of depositary institution | NPMD National Institute of Technology and Evaluation, Patent Microorganisms Depositary (NPMD) |
| 1-3-2 | Address of depositary institution | 2-5-8 Kazusakamatari, Kisarazu-shi, Chiba, JAPAN 292-0818 |
| 1-3-3 | Date of deposit | Feb. 29, 2008 |
| 1-3-4 | Accession Number | NPMD BP-514 |
| 1-4 | ADDITIONAL INDICATIONS | none |
| 1-5 | Designated states for which indications are made | All designated states |
| 1-6 | Separate furnishing of indications | none |
| | The indications listed in the right will be submitted to the International Bureau later. | |
| 2 | The indications made below relate to the microorganism or other biological material referred to in the Detailed Description of the Invention. | |
| 2-1 | Paragraph numbers | 0011, 0012, 0024 |
| 2-3 | IDENTIFICATION OF DEPOSIT | |
| 2-3-1 | Name of depositary institution | NPMD National Institute of Technology and Evaluation, Patent Microorganisms Depositary (NPMD) |
| 2-3-2 | Address of depositary institution | 2-5-8 Kazusakamatari, Kisarazu-shi, Chiba, JAPAN 292-0818 |
| 2-3-3 | Date of deposit | Feb. 29, 2008 |
| 2-3-4 | Accession Number | NPMD BP-515 |
| 2-4 | ADDITIONAL INDICATIONS | none |
| 2-5 | Designated states for which indications are made | All designated states |
| 2-6 | Separate furnishing of indications | none |
| | The indications listed in the right will be submitted to the International Bureau later. | |
| 3 | The indications made below relate to the microorganism or other biological material referred to in the Detailed Description of the Invention. | |
| 3-1 | Paragraph numbers | 0011, 0012, 0024 |
| 3-3 | IDENTIFICATION OF DEPOSIT | |
| 3-3-1 | Name of depositary institution | NPMD National Institute of Technology and Evaluation, Patent Microorganisms Depositary (NPMD) |
| 3-3-2 | Address of depositary institution | 2-5-8 Kazusakamatari, Kisarazu-shi, Chiba, JAPAN 292-0818 |
| 3-3-3 | Date of deposit | Feb. 29, 2008 |
| 3-3-4 | Accession Number | NPMD BP-516 |
| 3-4 | ADDITIONAL INDICATIONS | none |
| 3-5 | Designated states for which indications are made | All designated states |

| | | | |
|---|---|---|---|
| 3-6 | Separate furnishing of indications<br>The indications listed in the right will be submitted to the<br>International Bureau later. | none | |
| 4 | The indications made below relate to the deposited<br>microorganism or other biological material referred to in<br>the Detailed Description of the Invention. | | |
| 4-1 | Paragraph numbers | 0011, 0012, 0024 | |
| 4-3 | IDENTIFICATION OF DEPOSIT | | |
| 4-3-1 | Name of depositary institution | NPMD National Institute of<br>Technology and Evaluation,<br>Patent Microorganisms<br>Depositary (NPMD) | |
| 4-3-2 | Address of depositary institution | 2-5-8 Kazusakamatari,<br>Kisarazu-shi, Chiba, JAPAN<br>292-0818 | |
| 4-3-3 | Date of deposit | Feb. 29, 2008 | |
| 4-3-4 | Accession Number | NPMD BP-517 | |
| 4-4 | ADDITIONAL INDICATIONS | none | |
| 4-5 | Designated states for which indications are made | All designated states | |
| 4-6 | Separate furnishing of indications<br>The indications listed in the right will be submitted to the<br>International Bureau later | none | |

For Receiving Office Use Only

For International Bureau Use Only

| | | | | |
|---|---|---|---|---|
| 0-4 | This sheet was received with the international<br>application (yes/no) | | 0-5 | Date received by the International Bureau |
| 0-4-1 | Authorized officer | | 0-5-1 | Authorized officer |

The invention claimed is:

1. A method for producing a *Kluyveromyces marxianus* transformant having a flocculation property and thermotolerance comprising the following steps (A) to (C) sequentially:
   (A) a step of producing *Saccharomyces cerevisiae* transformant by introducing a marker gene sequence and an expression promoter sequence in the upstream of at least one FLO gene selected from endogenous FLO1 gene and endogenous FLO9 gene of *Saccharomyces cerevisiae*;
   (B) a step of obtaining a DNA fragment containing the marker gene sequence, expression promoter sequence, and FLO gene sequence from a chromosomal DNA derived from the *Saccharomyces cerevisiae* transformant produced in step (A); and
   (C) a step of producing a *Kluyveromyces marxianus* transformant by introducing the DNA fragment obtained in step (B) into *Kluyveromyces marxianus* as a FLO gene expression cassette.

2. The method for producing a *Kluyveromyces marxianus* transformant according to claim 1, wherein the marker gene is an auxotrophic marker gene.

3. The method for producing a *Kluyveromyces marxianus* transformant according to claim 2, wherein the auxotrophic marker gene is at least one auxotrophic gene related to a production of histidine, leucine, uracil, methionine, lysine, adenine, tryptophan or arginine.

4. The method for producing a *Kluyveromyces marxianus* transformant according to claim 3, wherein the auxotrophic marker gene is URA3 gene.

5. The method for producing a *Kluyveromyces marxianus* transformant according to any one of claims 1 to 4, wherein the *Kluyveromyces marxianus* is a *Kluyveromyces marxianus* mutant having a mutation in at least one auxotrophic gene related to a production of histidine, leucine, uracil, methionine, lysine, adenine, tryptophan or arginine.

6. The method for producing a *Kluyveromyces marxianus* transformant according to claim 1, wherein the expression promoter is the glyceraldehyde-3-phosphate dehydrogenase3 promoter from the TDH3 gene.

7. The method for producing a *Kluyveromyces marxianus* transformant according to claim 1, comprising introducing a linear DNA fragment into *Kluyveromyces marxianus* as a FLO gene expression cassette.

8. The method for producing a *Kluyveromyces marxianus* transformant according to claim 1, wherein the *Kluyveromyces marxianus* transformant is RAK4299 strain (NITE BP-514) or RAK4301 strain (NITE BP-516).

9. A *Kluyveromyces marxianus* transformant having a flocculation property and thermotolerance produced by the production method according to claim 1.

10. The *Kluyveromyces marxianus* transformant according to claim 9 which is RAK4299 strain (NITE BP-514) or RAK4301 strain (NITE BP-516).

* * * * *